United States Patent [19]

Weichselbaum

[11] 3,976,529

[45] Aug. 24, 1976

[54] METHOD OF SEALING FILTER IN TUBULAR FITTING FOR MEDICAL INJECTION EQUIPMENT AND THE LIKE

[75] Inventor: Theodore E. Weichselbaum, Normandy, Mo.

[73] Assignee: Sherwood Medical Industries Inc., St. Louis, Mo.

[22] Filed: Jan. 31, 1974

[21] Appl. No.: 438,298

Related U.S. Application Data

[62] Division of Ser. No. 323,726, Jan. 15, 1973, Pat. No. 3,817,389.

[52] U.S. Cl.............................. 156/272; 128/214 R; 156/275; 156/294; 210/448; 210/452; 210/510; 219/10.53
[51] Int. Cl.².................... B01D 39/20; B29C 27/04
[58] Field of Search ........... 156/272, 293, 294, 273, 156/275; 210/448, 446, 451, 452, 496, 510, DIG. 23, 214 R; 219/8.5, 10.41, 10.43, 10.53; 128/214 B, 214 C, 221, 276

[56] References Cited
UNITED STATES PATENTS

| | | | |
|---|---|---|---|
| 2,566,354 | 9/1951 | Morey............................. | 210/510 X |
| 2,915,187 | 12/1959 | Jaffe ................................ | 210/451 X |
| 2,982,418 | 5/1961 | Balley................................ | 210/448 |
| 3,121,685 | 2/1964 | Hazell............................. | 210/496 X |
| 3,406,831 | 10/1968 | Bush et al........................ | 210/489 X |
| 3,583,458 | 6/1971 | Costa................................ | 219/8.5 X |
| 3,722,697 | 3/1973 | Burke et al. ........................ | 210/451 |

Primary Examiner—Douglas J. Drummond
Assistant Examiner—M. G. Wityshyn
Attorney, Agent, or Firm—Gardner and Anten

[57] ABSTRACT

A cylindrical, cup-shaped, porous, sintered powdered metal filter is sealed in a tubular thermoplastic fitting (e.g., the needle-retaining hub of a hypodermic needle or an adaptor or a connector in the line of an intravenous infusion set) by force-fitting the open end of the filter within an annular bead on the interior wall of the tubular fitting and induction heating the filter so that the thermoplastic bead will flow into the pores of the filter to form a continuous ring seal between the filter and the interior wall of the fitting.

4 Claims, 5 Drawing Figures

METHOD OF SEALING FILTER IN TUBULAR FITTING FOR MEDICAL INJECTION EQUIPMENT AND THE LIKE

This is a divisional of application Ser. No. 323,726, filed Jan. 15, 1973, now U.S. Pat. No. 3,817,389.

The present invention relates generally to medical equipment and, more specifically, to filter devices for use in medical injection equipment such as hypodermic needles and intravenous infusion sets.

In recent years medical researchers have been expressing increasing concern about the presence of particulate contamination in parenteral solutions intravascularly infused or injected into patients, and about the possible harm such contamination may cause. The term "parenteral solutions" as used throughout this patent is intended to refer to any solution intravenously or intramuscularly fed to a patient, including medication injected by a hypodermic syringe and various solutions (e.g., glucose, blood, medication, et cetera) fed intravenously through an intravenous infusion set.

It is estimated that the average hospital patient currently receives approximately 2.5 liters of parenteral solutions during his illness, and the critically ill patient may receive as much as 100 liters or more. Recent studies have shown that the parenteral solutions are often contaminated by particulate matter from the infusion equipment, e.g., the glass or plastic container for the solution, the tubing set, the stopper or bung and other accessories of the equipment. Obviously such contamination may be harmful to the patient, depending on the type, size, quantity, etc., of the contaminating particles. Harmful effects have been demonstrated by medical researchers by means of human autopsies and studies on various animals.

Particulate contamination is also present in the parenteral solutions injected into patients by means of hypodermic syringes. Sources of such contamination include the syringe barrels, plungers (which typically have rubber tips) and the covers (typically rubber) and interior (typically glass) of multi-dose vials from which solutions to be injected are withdrawn.

It is thus apparent that there is a need in the medical field for some means to prevent or minimize particulate matter contamination in parenteral solutions.

It has been suggested that filters be employed in injection equipment to filter particulate contamination from parenteral fluids fed to patients. However, no filters or filter devices heretofore designed have met with any appreciable acceptance or use in the medical field because none of these prior filter devices have satisfied various requirements that any filter employed in conjunction with medical injection equipment must meet. One such requirement is that the filter element must be effectively sealed or bonded in the fluid flow line of the injection or infusion equipment to insure that the filter performs its intended function effectively and efficiently.

A second requirement is that the filter device and means of incorporation into the injection or infusion equipment not add appreciably to the cost of the equipment, particularly in view of the fact that most of the injection and infusion equipment in use today is disposable (i.e., designed to be discarded after a single use).

A tird important requirement is that the filter must be compatible with the shape, size and operation of existing injection and infusion equipment.

The filter device of the present invention, and the method of making the device satisfy the efficiency, cost and compatibility requirements discussed above, and provide other advantages which will become apparent from a review of the filter device and method of the present invention as shown in the drawings and described in the following specification and claims.

Figure 1:
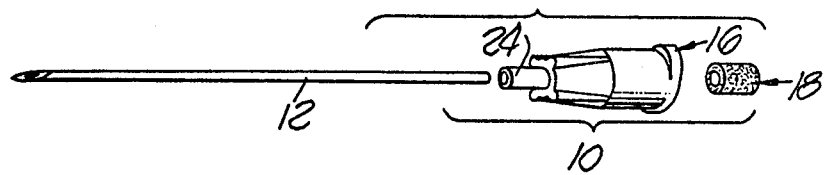
FIG. 1 is an exploded perspective view of a hypodermic needle into which a filter device of the present invention may be incorporated.

FIG. 1 illustrates a hypodermic needle 10 into which the filter device of the present invention may be incorporated. The needle 10 includes a needle cannula 12 (preferably stainless steel) connected to the forward or distal end of a thermoplastic tubular hub or fitting 16 having a porous, sintered, powdered metal filter element 18 therein. The hypodermic needle 10 of FIG. 1 is only an exemplary showing of a medical injection device into which the filter device of the present invention may be incorporated. It is contemplated that the filter device of the present invention may be incorporated in various types of medical equipment and the like, including intravenous infusion sets, hypodermic syringes and double luer adapters. The tubular thermoplastic fitting or connector 16 is exemplary of only one of numerous types of connectors, fittings, adaptors and hubs into which a filter may be incorporated and sealed to form the filter device of the present invention.

The structure of the filter device of the present invention and the method by which the porous metal filter 18 is sealed into the tubular thermoplastic connector 16 to form a filter device of the present invention may best be understood by referring to FIGS. 2 to 5.

The thermoplastic connector 16 is of generally tubular shape and has internal peripheral wall 19 defining a longitudinal passage 20 extending therethrough. The outer or proximal end 22 of the passage 20 is tapered outwardly (commonly referred to in the medical field as a female luer taper) to facilitate sealing reception of the tip of a syringe (or other tubular member) to which the proximal end of the fitting 16 is to be connected. The forward or distal end of the passage through the stem 24 may be cylindrical or tapered to receive the butt end of the needle cannula 12, which may, for example, be epoxy bonded therein.

The intermediate portion of the peripheral wall 19 of passage 20 is provided with a shoulder 30 which functions as a seat for the end of the filter 18. An inwardly-projecting annular ring or bead 32 is provided on the interior wall 19 of the fitting 16 just above the shoulder or seat 30. The internal diameter of the bead 32 is slightly less than the outer diameter of the filter 18 so that the end of the filter 18 can be force-fit into the bead 32 in a manner and for a purpose described more fully below.

The term thermoplastic, as used herein, is intended to refer to any plastic material that will soften when heated and re-solidify or harden when cooled. The thermoplastic fitting or connector 16 is preferably constructed of a relatively rigid thermoplastic such as polypropylene, polycarbonate or polyethylene terephtnalate.

The filter 18 is preferably cylindrical cup-shaped in form, having a closed rear end 36 and an open forward end 38 defined by a forward peripheral wall 39.

The filter 18 is preferably formed of a porous, sintered, powdered stainless steel. The particular formation and interrelationship of the particles of the filter 18 are important, but do not constitute a part of the invention of this patent. The filter 18 may be made in accordance with the teachings of U.S. Pat. No. 3,933,652.

The filter element 18 is positioned and sealed or bonded in the tubular fitting 16 in the following manner.

Figure 2:
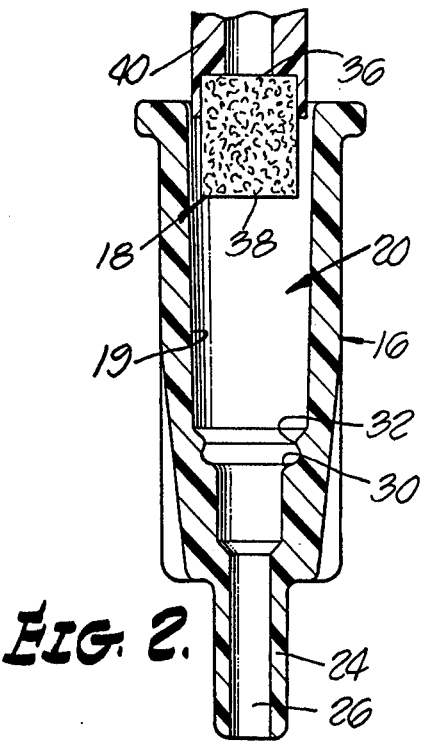
FIG. 2 is a sectional elevation view of the hub or tubular fitting of the apparatus shown in FIG. 1 with a filter element of the present invention being inserted therein.
Figure 3:
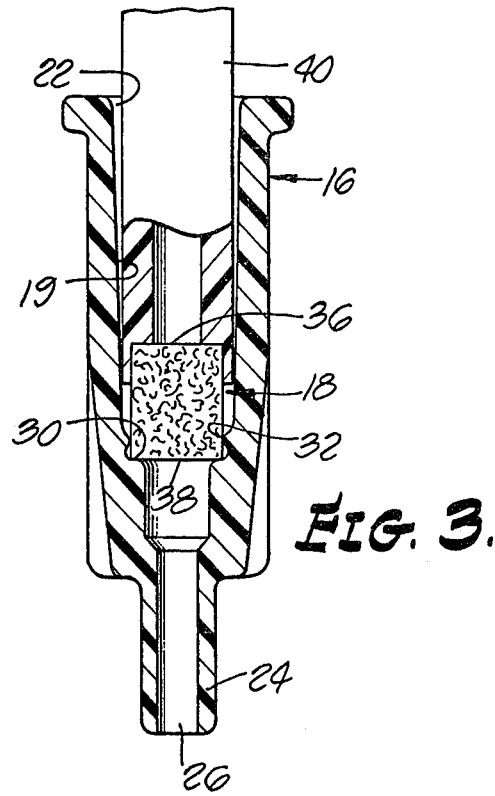
FIG. 3 is a sectional elevation view similar to FIG. 2 showing the filter in place in the fitting.

The filter element 18 is inserted, open end first, into the passage 20 of the fitting 16 by means of a suitable tool, such as the insertion tip 40 of a suitable vacuum tool, as shown in FIG. 2. The filter element 18 is held on the tool 40 by suction, and is pressed downwardly through the plastic annular ring or bead 32 until the forward peripheral wall 39 of the open forward end 38 rests or seats on the annular shoulder 30. As noted above, the outer diameter of the filter element 18 is slightly larger than the internal diameter of the annular bead 32 so that the forward end of the filter 18 is force-fit in the annular bead 32 to compress and deform the bead (see FIG. 3).

Figure 4:
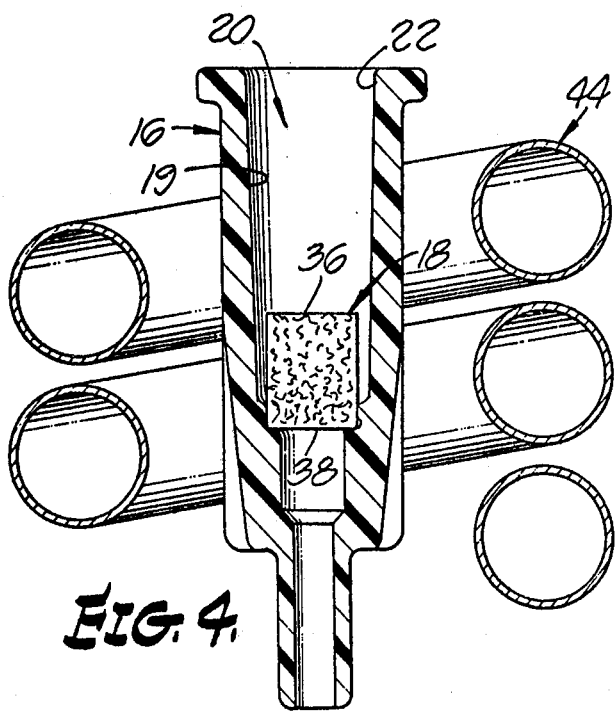
FIG. 4 is a sectional elevation view similar to FIGS. 2 and 3 showing the filter being induction heated to seal it in the fitting.

With the filter element 18 in place (i.e., with the forward end wall 39 of the filter abutting the shoulder 30 in the fitting 16 and the forward end portion of the peripheral wall of the filter 18 force-fit in the annular bead 32), the filter element 18 is heated to a temperature and for such a time to heat the thermoplastic bead 32, which melts or softens and flows into the pores in a continuous ring around the forward end portion of the outer peripheral wall of the filter element 18. As shown in FIG. 4, it is contemplated that the filter element 18 may be heated by the electromagnetic field generated by induction heating coils 44. It is contemplated, however, that other means of heating the filter element 18 may be employed so long as such heating means does not interfere with the compressive force exerted by the filter element on the annular bead 32.

Figure 5:
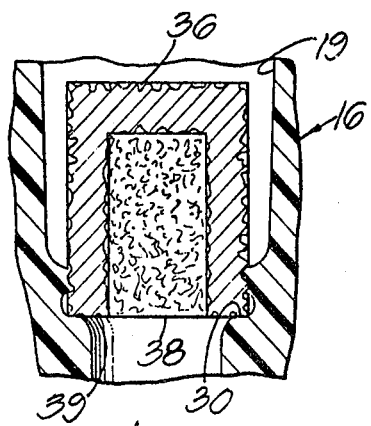
FIG. 5 is a partial sectional elevation view showing in greater detail the seal between the filter and the fitting.

FIG. 5 is an enlarged sectional view illustrating the intrusion of the plastic bead 32 into the pores around the outer peripheral wall of the forward end portion of the filter element 18 after the bead has cooled and re-solidified.

It is to be noted that the seal or bond formed between the bead 32 and the forward end portion of the outer surface of filter element 18 is a relatively thin continuous ring which does not significantly reduce the effective surface area of the filter which is exposed to the solution to be filtered. Thus, the seal will not inhibit the flow rate of the solution which must pass through the filter. It is to be noted that the foregoing is a significant advantage of the present invention because it is essential to maintain the effective surface area of the filter element 18 at a maximum to insure that the flow rate of the solution passed through the filter may be maintained at the desired level. It will also be noted that the cylindrical cup shape of the filter element 18 maximizes the effective surface area of the filter which is exposed to the solution to be passed therethrough, consistant with the over-all size limitations imposed by the fitting into which it is inserted, to maximize the permissible flow rate of the solution.

From the foregoing, it will be appreciated that the method of the present invention provides a filter device for medical injection equipment and the like which is relatively inexpensive, efficient and readily adaptable for use with existing injection and infusion equipment (e.g., plastic fittings, such as injection needle hubs). The ring seal or bond formed between the tubular fitting and the peripheral wall of the filter provides an effective continuous seal which does not interfere with the critical, permissible flow rate of solution through the filter, yet insures a fluid tight seal to prevent fluid from passing around, rather than through, the filter element. Thus, the method and resulting filter device of the present invention satisfies the existing need in the industry for a device which will effectively eliminate or minimize particulate contamination in parenteral fluids to be injected into patients.

It is contemplated, of course, that numerous changes and modifications may be made to the particular embodiments of the method and filter device described above and shown in the drawings without departing from the scope of the present invention. For example, while a cylindrical cup-shaped filter has been shown and described as a preferable embodiment, it is contemplated that method and filter devices of the present invention may employ filter elements of other shapes, such as disk shapes, plate shapes and rounded cup shapes.

Accordingly, it is intended that the scope of the present invention be limited only by the scope of the appended claims.

I claim:

1. A method of making a filter device for medical infusion and injection equipment and the like, comprising the steps of: inserting an at least partially metallic porous filter element into an open area defined by a peripheral portion of the interior peripheral wall of an at least partially plastic peripheral member so that the outer periphery of the filter engages and contacts said peripheral portion of said interior peripheral wall along a continuous peripheral ring; and heating said filter element to a temperature sufficient to cause said peripheral portion of the interior peripheral wall of said peripheral member to flow into the pores of said filter element and thereby create a seal between the filter element and the interior peripheral wall along a continuous peripheral ring said filter element comprising a sintered, powdered, metal filter body.

2. A method of making a filter device for medical infusion and injection equipment and the like, comprising the steps of: force fitting a porous metallic filter element into a plastic, annular projection within the interior peripheral wall of a tubular member, and heating said filter element to a temperature sufficient to cause a peripheral portion of the interior peripheral wall of said plastic annulus to soften and flow into pores in said porous filter element to form a continuous peripheral seal between said tubular member and said filter element said filter element comprising a sintered, powdered, metal filter body.

3. A method of making a filter element according to claim 2, wherein said step of heating said filter element comprises induction heating said filter element by means of the electromagnetic field generated by an induction coil surrounding said filter element and said tubular member.

4. A process for making a filter for medical injection equipment and the like, comprising:

positioning a sintered, porous, powdered metal filter body having a surface and a peripheral wall depending therefrom into an annular, thermoplastic member;

applying compressive force to the area of contact of said peripheral wall and the interior of said annular member;

heating, while maintaining said compressive force, said filter body and said annular thermoplastic member to a temperature such that the thermoplastic flows into pores of said peripheral wall; and cooling said filter body and said annular member to obtain a liquid seal at the area of contact.

* * * * *